United States Patent [19]

Fujii et al.

[11] Patent Number: 5,093,130
[45] Date of Patent: Mar. 3, 1992

[54] POWDER COATED HYDROGEL CAPSULES

[75] Inventors: Jon A. Fujii; Keith Redenbaugh, both of Davis, Calif.; Yuji Sakamoto, Tochigi, Japan

[73] Assignee: Plant Genetics, Davis, Calif.

[21] Appl. No.: 412,846

[22] Filed: Sep. 26, 1989

[51] Int. Cl.⁵ .............................................. A61K 9/48
[52] U.S. Cl. ................................. 424/463; 424/195.1; 424/452; 424/455; 424/456; 424/600; 424/724; 424/93; 514/770; 514/772; 514/774; 514/778; 514/779; 514/780; 514/781; 514/782
[58] Field of Search .............. 424/463, 451, 452, 456, 424/459, 478, 410, 474, 405, 408

[56] References Cited

U.S. PATENT DOCUMENTS 2,853,421  9/1958  Adams et al. .................. 424/478
4,701,326  10/1987 Nelsen et al. .................. 424/410

Primary Examiner—Thurman K. Page
Assistant Examiner—James M. Spear
Attorney, Agent, or Firm—Limbach & Limbach

[57] ABSTRACT

Methods and materials are provided for coating hydrogel capsules containing botanic tissue with an inert substance that decrease capsule surface adhesiveness and facilitates singulation and flowability of the hydrogel capsules. The coating may be composed of at least one hydrophobic powder capable of forming a discontinuous film about the capsule surface.

7 Claims, No Drawings

POWDER COATED HYDROGEL CAPSULES

TECHNICAL FIELD

This invention relates to materials and methods for coating hydrogel capsules, and more particularly to applying coatings to hydrogel capsules which can decrease surface adhesiveness and facilitate capsule singulation.

BACKGROUND OF THE INVENTION

Hydrogels have been used for various purposes including the encapsulation of biological material such as organelles, enzymes, microorganisms and plant cells. See, e.g. K. Redenbaugh, D. Slade, P. Viss and M. Kossler, "Artificial seeds: encapsulation of somatic embryos," Forest and Crop Biotechnology—Progress and Prospects, F. Valentine, ed., Springer—Verlag, New York, pp. 400–419. U.S. Pat. Nos. 4,615,883 and 4,701,326 disclose the use of such structures to encapsulate nematodes and U.S. Pat. Nos. 4,562,663 and 4,583,320 describe systems utilizing encapsulated plant meristematic tissue.

The gel capsules disclosed, however, adhere together due to the sticky, adhesive nature of the capsule surface. As a result, capsules are not easily singulated into discrete units and are not readily flowable through automated planting machinery.

Mechanized planting requires the flow of individual capsules through the machinery used. The presence of aggregates or clumps tends to jam the feeding mechanism of the machinery and prevents mass handling of encapsulated plant units.

U.S. Pat. No. 4,715,143 discloses a method of singulation of hydrogel capsules using a membrane composed of various organic compounds or mixes of organic and inorganic compounds. The membrane compounds are first dissolved in various organic solvents and capsules are dipped into the membrane solution. The membrane produced forms a thin, continuous barrier over the capsule. This membrane suffers from several drawbacks. Capsules must be pre-treated before dipping in the membrane solution. The membrane is complicated to prepare and requires the exposure of encapsulated organisms to potentially toxic solutions. Further, the membrane components are subject to contamination during extended storage periods. In addition, the continuous barrier inhibits solute passage essential for leaching growth inhibitors and impedes gas exchange from the organism to the environment.

An alternative to using a solvent-based membrane system is the use of a hydrophobic powdered coating to allow for singulation of hydrogel capsules without the use of solvents or other organic compounds.

Hydrophobic powders have been used in various agricultural applications. U.S. Pat. No. 3,710,510 describes the use of pyrogenic silicas and metallic oxides dispersed in solution to form fine droplets of liquid coated with powder. These droplets can be added to planting beds of mineral solids such as sand, vermiculite, perlite and clays to accelerate seed germination rate and plant growth. U.S. Pat. No. 4,004,368 is a modification of this method for adhering the hydrophobic powders onto larger, heavier particles within the planting bed. Neither of these patents contemplate the use of powders for capsule singulation purposes.

Hydrophobic powders have also been used for coating seeds. U.S. Pat. No. 4,438,593 discloses the use of a particulate hydrophobe to enhance the effectiveness of anti-fungal agents against soil pathogens, but does not teach of the use of such powders for coating hydrogel capsules. Additionally, U.S. Pat. Nos. 4,583,320 and 4,715,143 describe the use of certain hydrophobic substances as a component of the hydrogel capsule. However, none of these references disclose the use of such substances as an adjunct to surround the hydrogel capsule to prevent capsule adhesion.

Accordingly, an object of this invention is to provide a technique whereby hydrogel capsules are coated with hydrophobic powders for singulation purposes.

Another object of the present invention is to provide a powder that does not absorb water and enables capsules to be flowable, single units.

Yet another object of the instant invention is to provide a powder coating that retains its ability to singulate capsules after extended storage periods.

A further object of the subject invention is to provide a coating that will not be degraded nor subject to contamination under septic storage conditions.

A still further object of the invention is the use of powders that are innocuous and non-toxic to the plant tissue encased within the capsules.

DISCLOSURE OF THE INVENTION

The present invention provides powder-coated, hydrated hydrogel capsules with decreased surface adhesiveness. Typically, such capsules are coated with hydrophobic powders to reduce surface adhesiveness and facilitate capsule singulation.

Also provided are methods for coating hydrated hydrogel capsules wherein selected powder coatings are applied to such capsules.

DETAILED DESCRIPTION OF THE INVENTION

In accordance with the invention, hydrated hydrogel capsules are produced with improved surface qualities by coating the capsules with selected powders subsequent to capsule formation. The invention also provides capsules coated with specific hydrophobic powders that do not absorb water. These powders prevent adherence of the hydrogel capsules to one another and therefore facilitate singulation.

Hydrogels capsules have been shown to be desirable for encapsulating plant meristematic tissue. See, e.g. K. Redenbaugh, D. Slade, P. Viss and M. Kossler, "Artificial seeds: encapsulation of somatic embryos," Forest and Crop Biotechnology—Progress and Prospects, F. Valentine, ed., Springer—Verlag, New York, pp. 400–419, and U.S. Pat. Nos. 4,562,663 and 4,583,320.

One anticipated advantage to such capsules is the ability to deliver exotic plant genotypes, especially those created through genetic manipulation, to field environments for growth with minimal alteration in conventional agricultural practices. In this manner, a successful analog to botanic seed should readily adapt to mechanical handling and planting.

However, it has been recognized that hydrogel capsules made from gels complexed with ionic solutions contain approximately 90% water and have tacky, or sticky surfaces. When stored, some of the contained water gradually evaporates from the capsule. Under refrigeration, this water collects and causes the capsules to adhere to one another. Consequently, the capsules cannot be easily singulated, are not readily flowable and tend to jam the feeding component of equipment such as mechanical planters.

The present invention provides powder-coated, hydrated hydrogel capsules with decreased surface adhesiveness. Typically, such capsules are coated with hydrophobic powders to reduce surface adhesiveness and facilitate capsule singulation.

Gels which have been found useful for encapsulating botanic tissue, solvents, solutes and other desirable adjuvants include sodium alginate, guar gum, carrageenan with locust bean gum, agar, carboxymethycellulose, gum tragacanth, sodium pectate, vinyl acetate, and sodium alginate with gelatin. Other suitable gels include, but are not limited to, those agents listed in Table 1.

TABLE 1

| | |
|---|---|
| I. Natural Polymers | |
| A. Ionic bonds (require complexing agents) | |
| Alginate with Gelatin | Furcellaran |
| Pectin | Hypnean |
| Dextran | Tamarind |
| Guar Gum | |
| B. Hydrophobic Interactions | |
| Amylose | Agarose |
| Agar with Gelatin | Gelatin |
| Starch | Amylopectin |
| Cornhull Gum | Starch Arabogalactan |
| Gum Ghatti | Gum Karagan |
| Ti Gum | Wheat Gum |
| Chitin | Dextrin |
| II. Chemically Modified Natural Polymers | |
| A. Ionic bonds (require complexing agents) | |
| Ethyl Succinylated Cellulose | Succinylated Zein |
| B. Hydrophobic Interactions | |
| Methylcellulose | Hydroxyethyl Cellulose |
| C. Covalent Bonds | |
| Gelatin with Glutaraldehyde | |
| III. Synthetic Polymers | |
| A. Covalent Bonds | |
| Polyacrylamide | |
| B. Hydrophobic Interactions | |
| Polyethylene Glycol | Polyvinylpyrrolidone |
| Polyoxyethylene | Hydrophilic Urethane |
| Polyvinylacetate | Vinyl Resins |
| Hydron (hydroxyethyl-methacrylate) | 2-methyl-5-vinylpyridine-methylacrylate-methacrylic acid |
| C. Ionic Bonds | |
| Sodium poly(styrene sulfonate) with poly(vinyl methyl pyridinium) chloride | |
| Sodium poly(styrene sulfonate) with poly(vinyl benzyl trimethyl ammonium) chloride | |
| Strongly acidic polyanion with strongly basic polycation | |
| Gelvatol ® (polyvinyl alcohol resin) (Monsanto) | |
| IV. Stabilizing Compounds | |
| A. Trade Names | |
| Super Slurper ® (USDA, SEA-AR, Nor. Reg. Res. Lab) | |
| Viterra ® (Union Carbide) | |
| Laponite ® (Laporte (United States) Inc.) | |
| Gelrite ® (Kelco) | |
| SeaKem ® (FMC Corporation) | |
| SeaPlaque ® (FMC Corporation) | |
| SeaPrep ® (FMC Corporation) | |
| IsoGel ® (FMC Corporation) | |
| B. Organic Compounds | |
| Lactose | Wax |
| Methylan Clear | Protein Colloids |
| Wallpaper Paste | |
| C. Inorganic Compounds | |
| Clay | |
| D. Inorganic Compounds that adhere by means of a water-soluble plastic such as methylcel: | |
| Fly Ash | Feldspar |
| Celrite | Bentonite |
| Vermiculite | Diatomaceous Earth |
| Lime | Calcium Carbonate |

Once the gel has been chosen for a particular application, there are numerous parameters which influence the characteristics previously mentioned.

A sodium alginate solution, for example, will form a water saturated gel when a complexing agent is added. Calcium chloride ($CaCl_2$) is generally used, however, lanthanum chloride, ferric chloride and cobaltous chloride, calcium nitrate, calcium hydroxide, superphosphate fertilizer, and many pesticides such as benefin, alachlor and chlorpropham are also acceptable, as are other multivalent cations.

An important factor which influences the choice of gel agent, and other parameters, is the choice of encapsulated material. In general, the coated hydrogel capsules of the present invention will find use as delivery systems for, e.g., living material including eukaryotic cells, microorganisms and botanic tissue including seed, somatic embryos, and other meristematic tissue capable of developing into an entire plant body. Alternatively, numerous adjuvants may be encapsulated within the capsules of the present invention, either separately or in combination with each other and with encapsulated living material.

A chosen gel will have a range of concentrations usable in working the invention. A concentration should be chosen to optimize ease of handling, gelling time, gel strength and coating thickness around the encapsulated material. If the gel is too dilute, the encapsulated material may settle during gel formation and produce an uneven encapsulation. The sodium alginate, for example, can be prepared in a concentration of 0.1 to 10% w(in grams)/v (in milliliters) in water, more usually 0.5 to 10% and ideally from 1 to 5%.

If seed is to be encapsulated, it can be added to the sodium alginate solution at a concentration of 1 to 50 seeds per milliliter, more usually from 1 to 10 seeds per milliliter. This concentration will vary as the appropriate size of the seeds varies with species and source.

Specific adjuvants to be encapsulated may be mixed with the sodium alginate at concentrations specific for the application rates of the particular adjuvants. The dispersed adjuvants in gel solution can then be added drop-wise to the complexing agent. Alternatively, the gel solution and complexing agent may be mixed by any of numerous techniques known to the art. These may include droplet formation and agent addition as a one step process by a vibrating nozzle which ejects a gel droplet from one source and coats the droplet with complexing agent from another.

The calcium chloride (or other complexing agent) may be made up in aqueous solution at a concentration of 1 to 1,000 millimolar, more usually 20 to 500 millimolar and ideally from 50 to 300 millimolar. Other complexing agents will have different preferred concentration ranges.

The time for gel formation and temperature of the gelling solutions are interrelated parameters, for selected concentrations of gel and complexing agent. The temperature should be chosen so as to avoid damage to botanic tissue, if present, usually in the range of 1° to 50°

C., more usually 10° to 40° C., and preferably at 20° to 40° C.

Within the range of acceptable temperatures, a particular value may be chosen to give the shortest possible gelling time consistent with complete gel formation. Typically, the gel will form immediately, but the complexation takes much longer. For a solution of sodium alginate at a concentration of 3.2 grams per 100 milliliters $H_2O$, calcium chloride solution at a concentration of 50 millimolar and 25° C. reaction temperature, adequate gelling is obtained in 5 to 120 minutes, more often 10 to 90 minutes and is usually sufficiently complete in 30 to 60 minutes. Alternatively, if 300 millimolar calcium chloride is substituted for 50 millimolar calcium chloride, gelling time is decreased to 2-5 minutes.

The gel characteristics described above are modifiable for each gel, but are determined generally by the concentration parameters and chemical properties of the gel.

Subsequent to capsule formation and prior to storage, the surface properties of the hydrogel capsule can be altered by use of the present invention. The encapsulated material can be coated with a powder that does not absorb water or absorbs water only at a slow rate. The powder will desirably be inert, non-toxic to encapsulated organisms and not susceptible to bacterial and fungal growth. Additionally, the powder should form a discontinuous film over the capsules thus allowing solute passage and gas exchange from the capsule into the environment. The powdered coating should not degrade during long storage periods. The coating should influence the handling properties of the capsule. Specifically, it should decrease surface adhesiveness and facilitate flowability of the capsule through automated planting devices. The presently preferred embodiment for such coating powders are hydrophobic powders.

Hydrophobic powder as used herein refers to particulate substances which do not absorb water or absorb water only at a slow rate. The particle size of powders used in the present invention may vary within wide limits, however, particles should be smaller than the hydrogel capsule to be coated so that a sufficient accumulation of powdered coating around the capsule can occur. Preferably, substances having a particle diameter of approximately 0.01 to 100 microns, preferably 0.1 to 1 micron will find use with the present invention. The particle shape can take on many of various forms including diamond-shaped, spherical, spheroidal or irregularly-shaped.

Suitable hydrophobic powders include but are not limited to polyvinylchloride granules, calcium stearate granules, magnesium stearate granules, talc and stearic acid. Also useful are fumed silica compounds such as CAB-O-SIL® HS-5, CAB-O-SIL® EH-5, and Tullanox® 500 (all from Tulco, Inc., Ayer, Mass.) as well as Nipsil® NS and Nipsil® E220A (Nippon Silika Kogyo Co. Ltd., Tokyo, Japan). Other suitable compounds include Aerosil® (a finely divided silicon dioxide, DeGussa, New York, N.Y.), aluminum silicate, metallic oxides such as titanium dioxide, various polyalcohols including cetyl alcohol and polyvinyl alcohol, cellulose and its derivatives such as Avicel® cellulose (a microcrystalline form of cellulose, Asahi Kasel Kogyo Co., Ltd., Japan), methylcellulose, ethylcellulose, and acetylcellulose.

In particular, Tullanox® 500, a proprietary product available from Tulco, Inc., Ayer, Mass., is a presently preferred embodiment for a powder of the present invention. It is described by the manufacturer as an inorganic powdered silica derived from a fumed silica base which is over 99.8% pure $SiO_2$. The hydrophilic hydroxyl groups which ordinarily populate the surface are replaced with organic trimethylsiloxyl groups. The hydroxyl groups which are present are so hindered stearically by the surrounding trimethylsiloxyl groups that they are unable to exhibit hydrophilic characteristics. According to the manufacturer, Tullanox® 500 has the following physical and chemical characteristics:

Nominal Particle Size—$0.007\mu$
Theoretical Surface Area—$325 m^2/g$
Bulk Density—3.01 bs./ft.$^3$
Specific Gravity—2.2
Refractive Index—1.76
Color—White
X-ray Form—Amorphous
pH (4% in 50/50 IPA/$H_2O$)—8-10
Surface Ammonia Content—0.2%

Some of the powders benefit from pretreatment prior to use. For instance, the fumed silica compounds should be aired before application. These compounds can be open-plate aired in a fume hood for six hours to one year, more usually 12 to 90 days, and ideally 18 hours to 30 days. Alternatively, the powder can be exposed to elevated temperatures of 50°-400° C., more usually 80°-300° C. and ideally 100°-200° C., for one minute to 100 days, more usually 5 minutes to 10 days and ideally 20 minutes to 24 hours.

The hydrogel capsule to be coated should be washed in water for approximately 20 minutes prior to powder application. Capsules containing botanic tissue can benefit from being soaked in $KNO_3$ subsequent to the water wash, at a concentration of 20-2000 mM, preferably 200-800 mM, for 30 seconds to 24 hours, more usually 5 minutes to 12 hours and ideally 10 minutes to 1 hour.

The desired hydrophobic powder is then applied to the treated capsules. Coating is accomplished by rolling the capsules in the powder for 1 second to 30 minutes, more usually 2 seconds to 5 minutes and ideally 5-60 seconds. Other suitable application methods include shaking or spraying the hydrophobic compounds onto the hydrogel capsules. The powdered substance adheres to the capsule by virtue of the inherent sticky nature of the surface of the hydrogel capsule. The coated hydrogel capsules thus formed possess the desired surface qualities, can be easily singulated and are flowable through mechanized planting equipment.

EXPERIMENTAL

In order to demonstrate the invention, the following experiments were carried out with a variety of coatings. All quantities labelled percent (%) are grams per 100 milliliters, unless otherwise indicated. All weights are given in grams (g) or milligrams (mg), all concentrations are given as millimolar (mM) or micromolar ($\mu M$) and all volumes are given in liters (L) or milliliters (mL) unless otherwise indicated.

EXAMPLE A (Coating Hydrated Hydrogel Capsules)

A.1. Coating with Polyvinylchloride Granules.

Hydrated hydrogel capsules were made by a dropwise addition of a 2% potassium alginate solution into 500 mL of 100 mM $Ca(NO_3)_2$ for 20 minutes to complex the alginate. The resulting capsules were washed in water for 20 minutes. The washed capsules were coated by rolling them in a dish of polyvinylchloride granules (Wako Pure Chemical Industries, Ltd., Osaka, Japan) for 30 seconds. The coated capsules were singulated and tested for flowability by adding them to a vibratory feeder (Count-A-Pak, Davis Tool and Engineering, Inc., Davis, Calif.). The vibratory feeder was activated and capsule movement and flowability were determined by the migration of the coated capsules up the feeder ramp. The polyvinylchloride granules provided a discontinuous coating over the capsules and the coated capsules continued to exhibit good flowability after 20 minutes of vibration. Uncoated alginate capsules did not migrate up the ramp.

A.2. Coating with Calcium Stearate

Hydrogel capsules were made and coated as in Example A.1 with the exception that calcium stearate granules (Wako Pure Chemical Industries, Ltd., Osaka, Japan) were substituted for the polyvinylchloride granules. The calcium stearate granules provided a suitable coating over the capsule and the coated capsules were singulated in a vibratory feeder as described in Example A.1.

A.3. Coating with Magnesium Stearate

Hydrogel capsules were made and coated as in Example A.1 with the exception that magnesium stearate granules (Wako Pure Chemical Industries, Ltd., Osaka, Japan) were substituted for the polyvinylchloride granules. The magnesium stearate granules provided a suitable coating over the capsule and the coated capsules were singulated in a vibratory feeder as described in Example A.1.

A.4. Coating with Avicel ® Cellulose

Hydrogel capsules were made and coated as in Example A.1 with the exception that Avicel ® cellulose (Asahi Kasei Kogyo Co., Ltd., Japan) was substituted for the polyvinylchloride granules. The Avicel cellulose provided a suitable coating over the capsules and the coated capsules were singulated in a vibratory feeder as described in Example A.1.

A.5. Coating with Methylcellulose

Hydrogel capsules were made and coated as in Example A.1 with the exception that methylcellulose (Wako Pure Chemical Industries, Ltd., Osaka, Japan) was substituted for the polyvinylchloride granules. The methylcellulose provided a suitable coating over the capsules and the coated capsules were singulated in a vibratory feeder as described in Example A.1.

A.6. Coating with Ethylcellulose

Hydrogel capsules were made and coated as in Example A.1 with the exception that ethylcellulose (Wako Pure Chemical Industries, Ltd., Osaka, Japan) was substituted for the polyvinylchloride granules. The ethylcellulose provided a suitable coating over the capsules and the coated capsules were singulated in a vibratory feeder as described in Example A.1.

A.7. Coating with Acetylcellulose

Hydrogel capsules were made and coated as in Example A.1 with the exception that acetylcellulose (Wako Pure Chemical Industries, Ltd., Osaka, Japan) was substituted for the polyvinylchloride granules. The acetylcellulose provided a suitable coating over the capsules and the coated capsules were singulated in a vibratory feeder as described in Example A.1.

A.8. Coating with Talc

Hydrogel capsules were made and coated as in Example A.1 with the exception that talc (Matsumura Sangyou Co., Ltd., Osaka, Japan) was substituted for the polyvinylchloride granules. The coated capsules were singulated and tested for flowability by adding them to a vibratory feeder (Vibra-flow Feeder F-OOB, Shinko Denki Kabushiki Kaisha, Tokyo, Japan). The vibratory feeder was activated and capsule movement and flowability were determined by the migration of the coated capsules up the feeder. The talc provided a discontinuous coating over the capsules and the coated capsules continued to exhibit good flowability for more than 20 minutes after coating. Uncoated alginate capsules did not migrate on the feeder.

A.9. Coating with Superfine Talc

Hydrogel capsules were made and coated as in Example A.8 with the exception that superfine talc (Super Cut #15, Freund Sangyou Co., Ltd., Tokyo, Japan) was substituted for the talc. The superfine talc provided a suitable coating over the capsules, and the capsules were singulated on the feeder as described in Example A.8.

A.10. Coating with Stearic Acid

Hydrogel capsules were made and coated as in Example A.8 with the exception that stearic acid (Wako Pure Chemical Industries, Ltd., Osaka, Japan) was substituted for the talc. The stearic acid provided a suitable coating over the capsules and the capsules were singulated on the feeder as described in Example A.8.

A.11. Coating with CAB-O-SIL ® EH-5

Hydrogel capsules were made and coated as in Example A.8 with the exception that CAB-O-SIL ® EH-5 (a fumed silica compound available from Tulco, Inc., Ayer, Mass.) was substituted for the talc. The CAB-O-SIL ® EH-5 provided a suitable coating over the capsules and the capsules were singulated on the feeder as described in Example A.8.

A.12. Coating with CAB-O-SIL ® HS-5

Hydrogel capsules were made and coated as in Example A.8 with the exception that CAB-O-SIL ® HS-5 (a fumed silica compound available from Tulco, Inc., Ayer, Mass.) was substituted for the talc. The CAB-O-Sil HS-5 provided a suitable coating over the capsules and the capsules were singulated on the feeder as described in Example A.8.

A.13. Coating with Tullanox ® 500

Hydrogel capsules were made and coated as in Example A.8 with the exception that Tullanox ® 500 (a fumed silica compound available from Tulco, Inc., Ayer, Mass.) was substituted for the talc. The Tullanox ® 500 provided a suitable coating over the capsules and the capsules were singulated on the feeder as described in Example A.8.

A.14. Coating with Nipsil ® NS

Hydrogel capsules were made and coated as in Example A.8 with the exception that Nipsil ® NS (Nippon Silika Kogyo Co., Ltd., Tokyo, Japan) was substituted for the talc. The Nipsil ® NS provided a suitable coating over the capsules and the capsules were singulated on the feeder as described in Example A.8.

A.15. Coating with Nipsil ® E220A

Hydrogel capsules were made and coated as in Example A.8 with the exception that Nipsil ® E220A (Nippon Silika Kogyo Co., Ltd., Tokyo, Japan) was substituted for the talc. The Nipsil E220A provided a suitable coating over the capsules and the capsules were singulated on the feeder as described in Example A.8.

A.16. Coating with Aerosil ®

Hydrogel capsules were made and coated as in Example A.8 with the exception that Aerosil ® (a finely divided silicon dioxide available from DeGussa, New York, N.Y.) was substituted for the talc. The Aerosil ® provided a suitable coating over the capsules and the capsules were singulated on the feeder as described in Example A.8.

A.17. Coating with Aluminum Silicate

Hydrogel capsules were made and coated as in Example A.8 with the exception that aluminum silicate (Wako Pure Chemical Industries, Ltd., Osaka, Japan) was substituted for the talc. The aluminum silicate provided a suitable coating over the granules and the capsules were singulated on the feeder as described in Example A.8.

A.18. Coating with Cetyl Alcohol

Hydrogel capsules were made and coated as in Example A.8 with the exception that cetyl alcohol was substituted for the talc. The cetyl alcohol provided a suitable coating over the granules and the capsules were singulated on the feeder as described in Example A.8.

EXAMPLE B (Coating Capsules Containing Tomato Seeds)

B.1 Coating with Tullanox ® 500

Tomato seeds, UC-82 (Garner Seed Co., Woodland, Calif.) were individually inserted into drops of 2% sodium alginate (Protan-Scotia Marine, Norway) and complexed by drop-wise addition of the alginate/seed mixture into 500 mL of 100 mM $Ca(NO_3)_2$. The encapsulated seeds were washed in water for 20 minutes and then soaked in 400 mM $KNO_3$ for 20 minutes. A portion of the encapsulated seeds were coated with Tullanox ® 500 (Tulco, Inc., Ayer, Mass.) which had been aired in an open dish in a fume hood for 24 hours. Capsules were coated by rolling in the aired Tullanox ® 500 for 30 seconds. The Tullanox ® 500 formed a hydrophobic coating around the hydrated, hydrogel capsule. A portion of the encapsulated seeds were not coated with the Tullanox ® 500.

Both the powder-coated and uncoated capsules were tested for flowability by rolling in an empty petri plate. The coated capsules rolled easily and exhibited high flowability. The uncoated capsules adhered in large aggregates and did not roll in the petri plate. Thus, the powdered coating was effective in singulation and increasing capsule flowability.

B.2 Coating with Tullanox ® 500

Powder-coated and uncoated capsules containing tomato seed were made as described in Example B.1, without the additional $KNO_3$ incubation, and tested for phytotoxicity by planting immediately after fabrication and coating in a soilless greenhouse potting mix (McCalif Growers Supplies, Inc., San Jose, Calif.) contained within an aluminum pan. The pan was placed in an incubator at 25° C. for 14 days and the total number of plantlets counted. Both the coated and uncoated capsules germinated at a frequency of 93%. Thus, the powdered coating appeared to have no effect on tomato seed germination.

B.3 Coating with Tullanox ® 500

Powder-coated and uncoated capsules containing tomato seed were made as in Example B.1, without the additional $KNO_3$ incubation, and tested for phytotoxicity after three weeks storage at 24° C. in closed bags. The stored capsules were planted and germinated as in Example B.2. The germination rates for powder-coated and uncoated capsules were similar, indicating that long-term contact of the powdered coating with the encapsulated seed did not have any detrimental effects on seed viability.

B.4 Coating with Tullanox ® 500

Powder-coated and uncoated capsules containing tomato seed were made as in Example B.1, without the additional $KNO_3$ incubation, and tested for flowability after 3 weeks storage at 24° C. in closed bags. After storage, the capsules had exuded some water but the coated capsules still retained good flowability whereas the uncoated capsules were not flowable.

B.5 Coating with Tullanox ® 500

Coated and uncoated capsules containing tomato seed were made as in Example B.1 and planted in a field using a cone planter. Cone planters are not designed to singulate capsules. Germination rates for the powder-coated and uncoated capsules were similar indicating that the powder-coating had no effect on field germination of encapsulated tomato seeds.

B.6 Coating with Tullanox ® 500

Coated and uncoated capsules containing tomato seeds (Heinz 7149, H.J. Heinz Company, Stockton, Calif.) were made as in Example B and tested for singulation. The coated capsules were easily planted in a field using a Stanhay planter (Hestair Farm Equipment, Ltd., Newmarket, England) which singulates seeds during the planting process. Uncoated capsules did not singulate well in the Stanhay planter. Thus the powdered coating enabled the use of automated planting machinery. Germination of the coated and uncoated capsules was similar indicating that the powder used had no effect on field germination of encapsulated tomato seeds.

Thus, methods for improving the surface properties of a hydrated hydrogel have been disclosed. As the aforementioned examples illustrate, the present invention facilitates singulation of the hydrated hydrogels by preventing the adherence of the capsules to one another. This in turn permits the capsules to be used with modern planting machinery.

Although the foregoing invention has been described in some detail by way of illustration for purposes of clarity of understanding, it will be obvious to those skilled in the art that numerous changes and modifications may be practiced within the spirit and scope of the appended claims.

We claim:

1. A hydrated gel capsule comprising biological material discontinuously coated with a powdered substance permeable to air and water and capable of reducing capsule surface adhesiveness thereby facilitating capsule singulation, wherein the capsule further comprises a gel matrix comprising at least one agent selected from the group consisting of sodium alginate, guar gum, carrageenan with locust bean gum, sodium alginate with gelatin, carboxymethylcellulose, gum tragacanth, sodium pectate, vinyl acetate, Furcellaran, pectin, hypnean, dextran, tamarind, amylose, agar, agarose, agar with gelatin, starch, amylopectin, cornhull gum, starch arabogalactan, gum ghatti, gum karagan, Ti gum, wheat gum, chitin, dextrin, ethyl succinylated cellulose, succinylated zein, methylcellullose, hydroxyethyl cellulose, gelatin with glutaraldehyde, polyacrylamide, polyethylene glycol, polyvinylpyrrolidone, polyoxyethylene, hydrophillic urethane, polyvinylacetate, vinyl resins, hydroxyethylmethacrylate, 2-methyl-5-vinylpyridine-methylacrylate-methylacrylic acid, sodium polystyrene sulfonate with polyvinylmethylpyridinium chloride, sodium polystyrene sulfonate with polyvinylbenzyltrimethylammonium chloride, strongly acidic polyanions with strongly basic polycations, vinyl acetate homopolymer, polyvinyl alcohol resin, a stabilizing carbohydrate compound, methylan clear wallpaper paste, lactose, wax, clay, fly ash, feldspar, celrite, bentonite, vermiculite, diatomaceous earth, lime, calcium carbonate, calcium oxide, magnesium carbonate, sodium bicarbonate and urea.

2. Botanic tissue encapsulated in a hydrogel, said hydrogel further coated with at least one hydrophobic powder selected from the group consisting of polyvinylchloride granules, calcium stearate granules, magnesium stearate granules, talc, stearic acid, fumed silica, pyrogenic silica, finely divided silicon dioxide, silicon dioxide, aluminum silicate, cetyl alcohol, microcrystaline cellulose, ethylcellulose, methylcellulose, and acetylcellulose.

3. The hydrogel capsule of claim 2 wherein said powdered substance comprises fumed silica.

4. A method for encapsulating botanic tissue comprising:

encapsulating botanic tissue in a hydrated hydrogel capsule; and coating the capsule with at least one powder selected from the group consisting of polyvinylchloride granules, calcium stearate granules, magnesium stearate granules, talc, stearic acid, fumed silica, pyrogenic silica, finely divided silicon dioxide, silicon dioxide, aluminum silicate, cetyl alcohol, microcrystaline cellulose, ethylcellulose, methylcellulose, and acetylcellulose in an amount that is permeable to air and water and sufficient to reduce adhesiveness of the capsules.

5. The method of claim 4 wherein said powdered substance comprises fumed silica.

6. Botanic tissue encapsulated within a hydrated hydrogel capsule comprising a gel matrix comprising at least one agent selected from the group consisting of sodium alginate, guar gum, carrageenan with locust bean gum, sodium alginate with gelatin, carboxymethylcellulose, gum tragacanth, sodium pectate, vinyl acetate, Furcellaran, pectin, hypnean, dextran, tamarind, amylose, agar, agarose, agar with gelatin, starch, amylopectin, cornhull gum, starch arabogalactan, gum ghatti, gum karagan, Ti gum, wheat gum, chitin, dextrin, ethyl succinylated cellulose, succinylated zein, methylcellullose, hydroxyethyl cellulose, gelatin with glutaraldehyde, polyacrylamide, polyethylene glycol, polyvinylpyrrolidone, polyoxyethylene, hydrophillic urethane, polyvinylacetate, vinyl resins, hydroxyethylmethacrylate, 2-methyl-5-vinylpyridine-methylacrylate-methylacrylic acid, sodium polystyrene sulfonate with polyvinylmethylpyridinium chloride, sodium polystyrene sulfonate with polyvinylbenzyltrimethylammonium chloride, strongly acidic polyanions with strongly basic polycations, vinyl acetate homopolymer, polyvinyl alcohol resin a stabilizing carbohydrate compound, methylan clear wallpaper paste, lactose, wax, clay, fly ash, feldspar, celrite, bentonite, vermiculite, diatomaceous earth, lime, calcium carbonate, calcium oxide, magnesium carbonate, sodium bicarbonate and urea which is coated with a powdered substance comprising at least one powder selected from the group consisting of polyvinylchloride granules, calcium stearate granules, magnesium stearate granules, talc, stearic acid, fumed silica, pyrogenic silica, finely divided silicon dioxide, silicon dioxide, aluminum silicate, cetyl alcohol, microcrystaline cellulose, ethylcellulose, methylcellulose, and acetylcellulose in an amount that is permeable to air and water and sufficient to reduce capsule surface adhesiveness, thereby facilitating capsule singulation.

7. The hydrogel capsule of claim 6 wherein said powdered substance comprises fumed silica.

* * * * *

UNITED STATES PATENT AND TRADEMARK OFFICE
CERTIFICATE OF CORRECTION

PATENT NO. : 5,093,130
DATED      : Mar. 3, 1992
INVENTOR(S): Jo Ann Fujii, Keith Redenbaugh, Yuji Sakamoto It is certified that error appears in the above-identified patent and that said Letters Patent is hereby corrected as shown below:

On the Title Page

Change "Inventors: Jon A. Fujii" to --Inventors:

Jo Ann Fujii--

Signed and Sealed this

Eighth Day of June, 1993

Attest:

MICHAEL K. KIRK

*Attesting Officer*   Acting Commissioner of Patents and Trademarks